(12) United States Patent
Fluegel et al.

(10) Patent No.: US 7,353,059 B2
(45) Date of Patent: Apr. 1, 2008

(54) MEDICAL DEVICE WITH LOW EMI LEAKAGE

(75) Inventors: John P. Fluegel, Ramsey, MN (US); John M. Kruse, New Brighton, MN (US); Paul T. Simonette, Maple Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 400 days.

(21) Appl. No.: 10/871,584

(22) Filed: Jun. 18, 2004

(65) Prior Publication Data

US 2005/0283194 A1     Dec. 22, 2005

(51) Int. Cl.
*A61N 1/16* (2006.01)
(52) U.S. Cl. .......................... 607/2; 128/901; 128/908; 361/799; 361/818; 439/95; 439/101
(58) Field of Classification Search ............ 607/36–38, 607/100, 59–60; 128/908, 904, 901; 174/32; 361/142, 625, 818, 816, 799; 439/65, 95–96, 439/101, 607–610
See application file for complete search history.

(56) References Cited

U.S. PATENT DOCUMENTS

| | | | | |
|---|---|---|---|---|
| 4,362,899 A | * | 12/1982 | Borrill | ..................... 174/36 |
| 4,827,378 A | * | 5/1989 | Gillan et al. | ................. 361/818 |
| 5,527,348 A | * | 6/1996 | Winkler et al. | ................ 607/30 |
| 5,817,130 A | * | 10/1998 | Cox et al. | ........................ 607/5 |
| 6,016,084 A | * | 1/2000 | Sugimoto | ..................... 333/12 |
| 6,151,527 A | * | 11/2000 | Boutos | ......................... 607/138 |
| 6,600,101 B2 | | 7/2003 | Mazurkiewicz | ......... 174/35 MS |
| 2001/0033478 A1 | | 10/2001 | Ortiz et al. | .................. 361/818 |
| 2003/0227760 A1 | * | 12/2003 | Albayrak et al. | ............ 361/800 |

FOREIGN PATENT DOCUMENTS

JP     2002/347065     4/2002

OTHER PUBLICATIONS

Halliday & Resnick, "Physics: Part Two", Chapter 30: Capacitors and Dielectrics, John Wiley & Sons, c. 1978, p. 655.*

* cited by examiner

*Primary Examiner*—Carl Layno
(74) *Attorney, Agent, or Firm*—Daniel G. Chapik; Stephen W. Bauer

(57) ABSTRACT

A medical device is configured to attenuate emission of electromagnetic radiation and comprises a housing, a circuit assembly mounted in the housing, and a panel coupled to the housing and to the circuit assembly. The panel comprises a first conductive region on an interior surface of the panel that is configured to be capacitively coupled to the ground, an opening substantially adjacent to the first conductive region, a second conductive region on the interior surface that is configured to be coupled to ground, and a non-conductive region on the interior surface between the first conductive region and the second conductive region.

13 Claims, 6 Drawing Sheets

MEDICAL DEVICE WITH LOW EMI LEAKAGE

FIELD OF THE INVENTION

The present invention generally relates to medical devices, and more particularly to the reduction of electromagnetic interference (EMI) produced by such devices.

BACKGROUND OF THE INVENTION

As is well known, there is a growing trend to incorporate sophisticated electronics in order to improve and/or enhance diagnosis and therapy delivery to a patient. There are a variety of such devices, some of which may be implanted within a patient's body and others of which are deployed externally. In addition, the use of medical devices that communicate in a wireless fashion with other such devices is becoming more common and is advantageous in that the patient need not be tethered by wire connections.

Safety is a major concern in the design and use of medical devices that are either implanted or externally worn by a patient. To this end, comprehensive design criteria has been established to prevent the occurrence of unwanted electrical shocks that might potentially harm the patient. In contrast to the significant efforts expended to prevent such unintended electrical shock, current medical device designs do not provide a reliable means for minimizing the transmission of electromagnetic interference (EMI) produced by the circuitry within the medical device. Such interference can interfere with the operation of other medical devices which may be problematic if such devices have been implemented and deployed to sustain or monitor the medical condition of a patient on an acute or chronic basis.

Accordingly, it would be desirable to provide a medical device that is configured to protect a patient from unwanted electrical shock and at the same time reduce the amount of transmitted electromagnetic interference. It would also be desirable to provide a medical device that transmits less EMI but is still characterized by high reliability, ease of manufacturing, and cost effectiveness.

BRIEF SUMMARY OF THE INVENTION

According to an aspect of the invention there is provided a medical device configured to attenuate emission of electromagnetic radiation comprising a housing, a circuit assembly mounted in the housing, and a panel coupled to the housing and to the circuit assembly. The panel comprises a first conductive region on an interior surface of the panel that is configured to be capacitively coupled to ground, an opening substantially adjacent to the first conductive region, a second conductive region on the interior surface that is configured to be coupled to ground, and a non-conductive region on the interior surface between the first conductive region and the second conductive region.

According to a further aspect of the invention there is additionally provided at least one capacitor electrically coupled between the first and second conductive region, a conductive shield coupled to a connector plug for attenuating electromagnetic radiation, and a conductive clip for electrically coupling the conductive shield to the first conductive region.

BRIEF DESCRIPTION OF THE DRAWINGS

The present invention will hereinafter be described in conjunction with the accompanying drawings, wherein like reference numerals denote like elements.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding discussion or the following detailed description.

Figure 1:
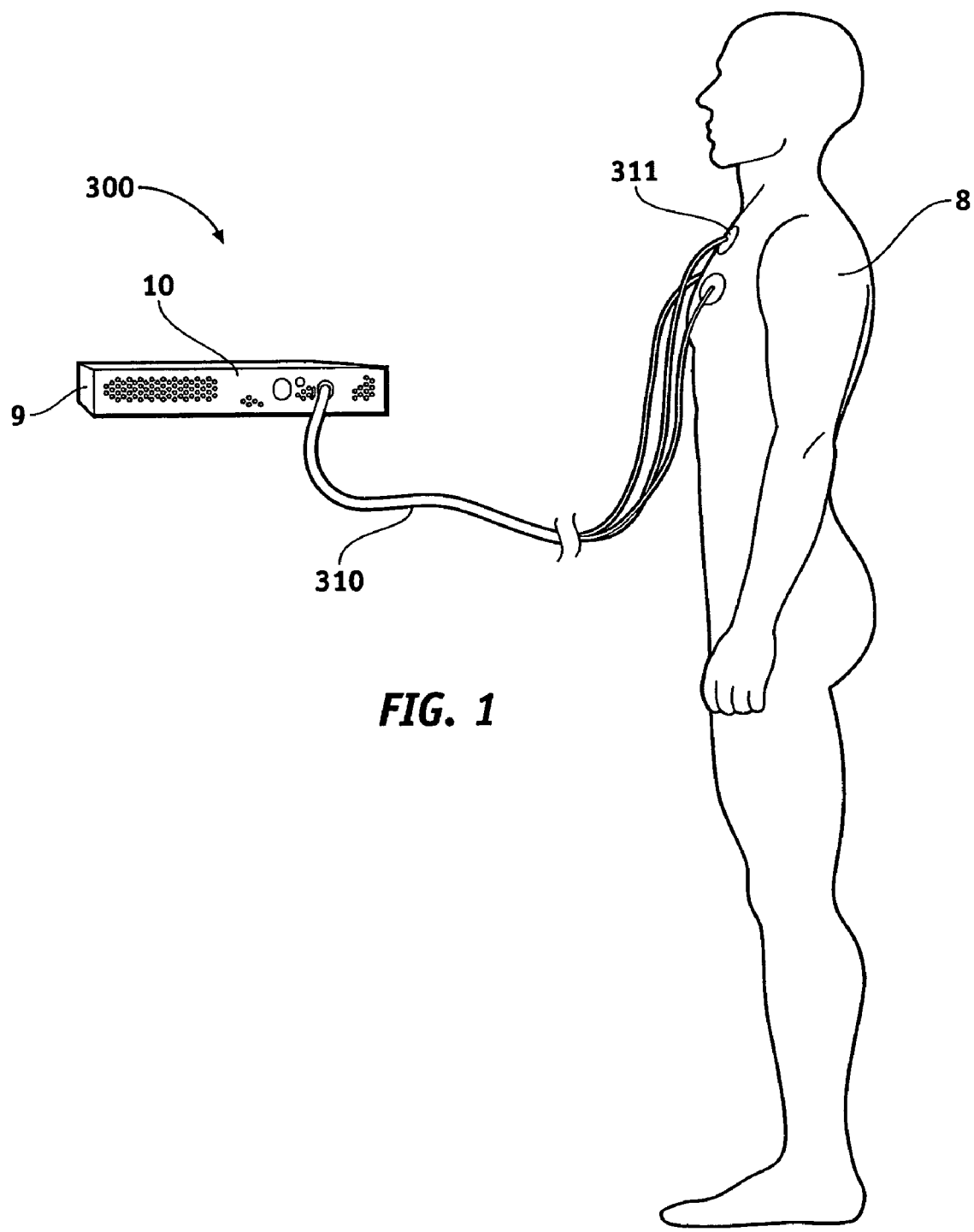
FIG. 1 illustrates a medical device including a cable and leads attached to a patient.

Referring to FIG. 1, a medical device 300 comprises an enclosure 9 and a rear panel 10 that together form a housing for containing the circuitry required to carry out the intended treatment. The therapy is delivered by medical device 300 by means of a cable 310 and plurality of electrodes 311 that are temporarily attached to a patient 8 as shown. Cable 310 is attached to the circuitry within the housing 9 by means of a connector assembly that will be more fully described hereinbelow.

The housing found by enclosure 9 and rear panel 10 protects the internal circuitry of the medical device 300 from the external environment including electromagnetic interference (EMI) produced by other external devices in close proximity. In return, the housing is grounded so as to attenuate electromagnetic radiation emitted by the circuitry within the medical device. As will be described below, the medical device's internal circuitry is equipped with a connector that may be electrically coupled to a complimentary connector on the end of cable 310 through an opening in rear panel 10. The internal connector is provided with a conductive shield that is AC coupled to ground. This arrangement has been shown to substantially reduce the electromagnetic interference transmitted from medical device 300.

Figure 2:
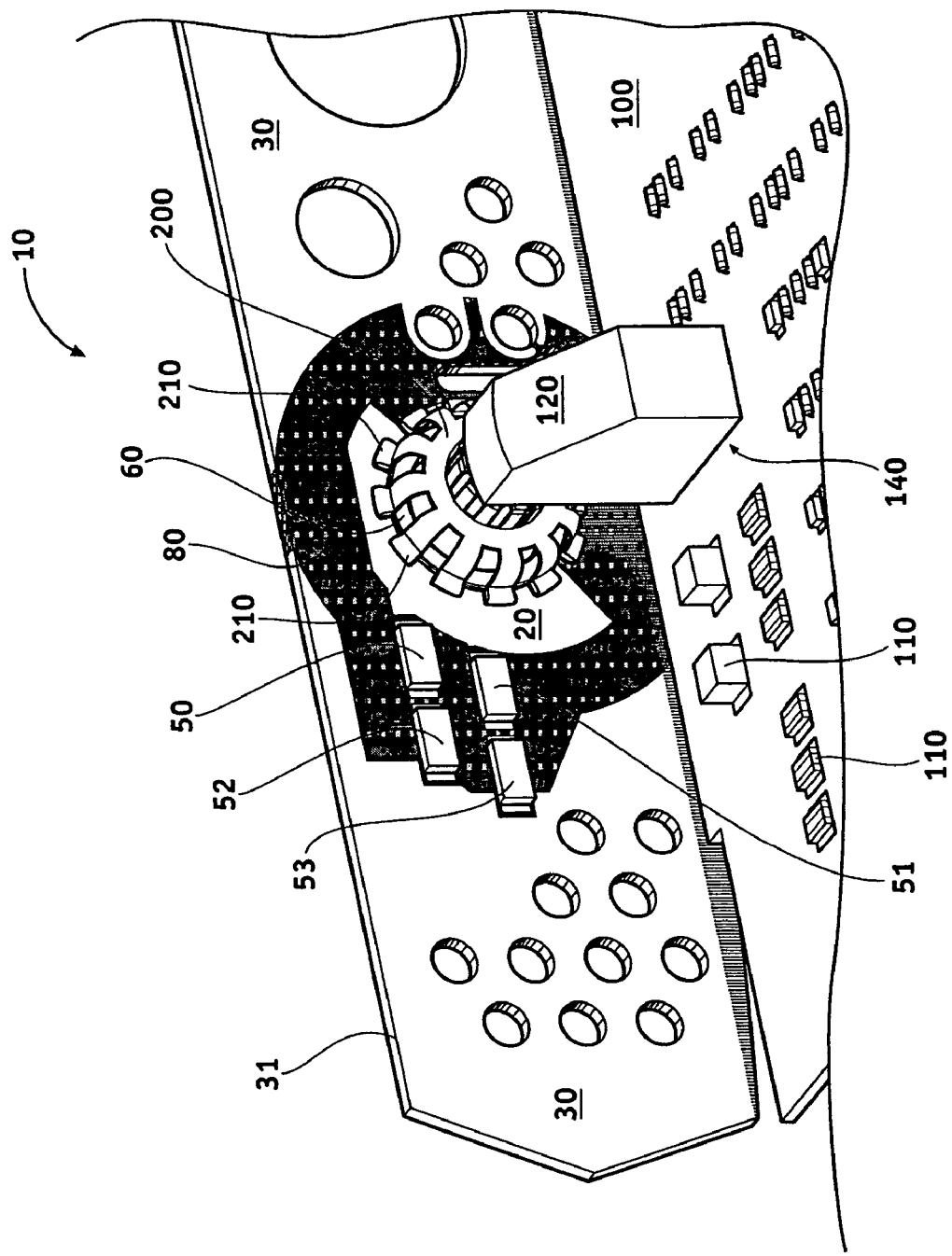
FIGS. 2 and 3 are isometric views illustrating a portion of the interior of the medical device shown in FIG. 1 in accordance with the present invention.
Figure 3:
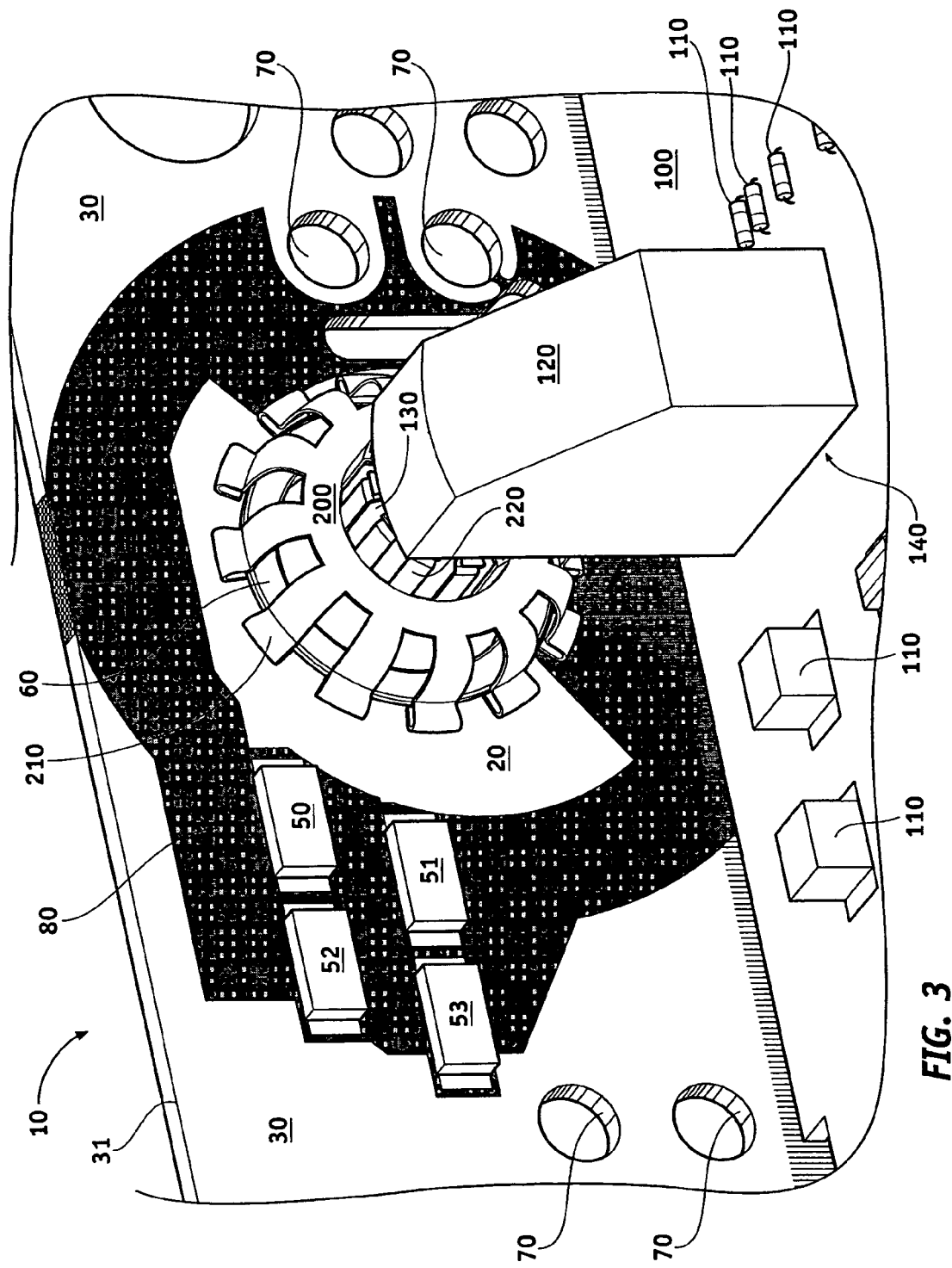

FIGS. 2 and 3 are isometric views of a portion of the interior of device 300 that illustrate panel 10, a substrate or printed circuit board 100 having a plurality of electrical components 110 thereon that together form the circuitry necessary to provide the required therapy, a connector 140 electrically coupled to the circuitry on printed circuit board 100, and a clip 200. Each of these components will be described in more detail in conjunction with FIGS. 4, 5, 6, and 7.

Figure 4:
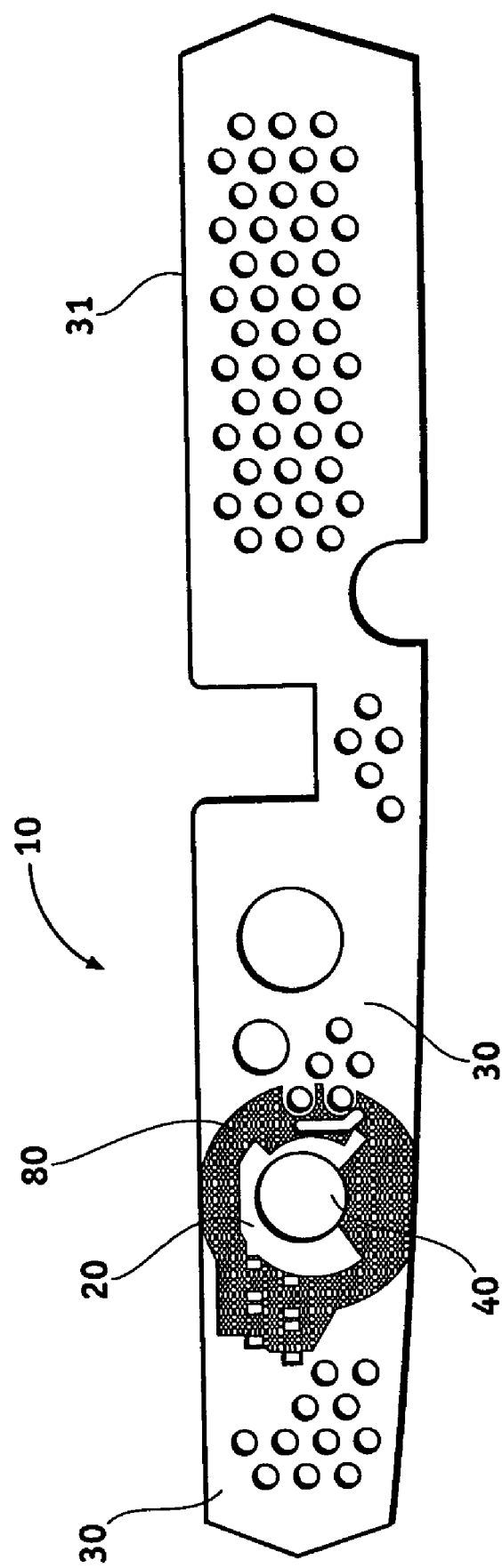
FIGS. 4 and 5 are plan and isometric views respectively of a panel shown in FIGS. 2 and 3.
Figure 5:
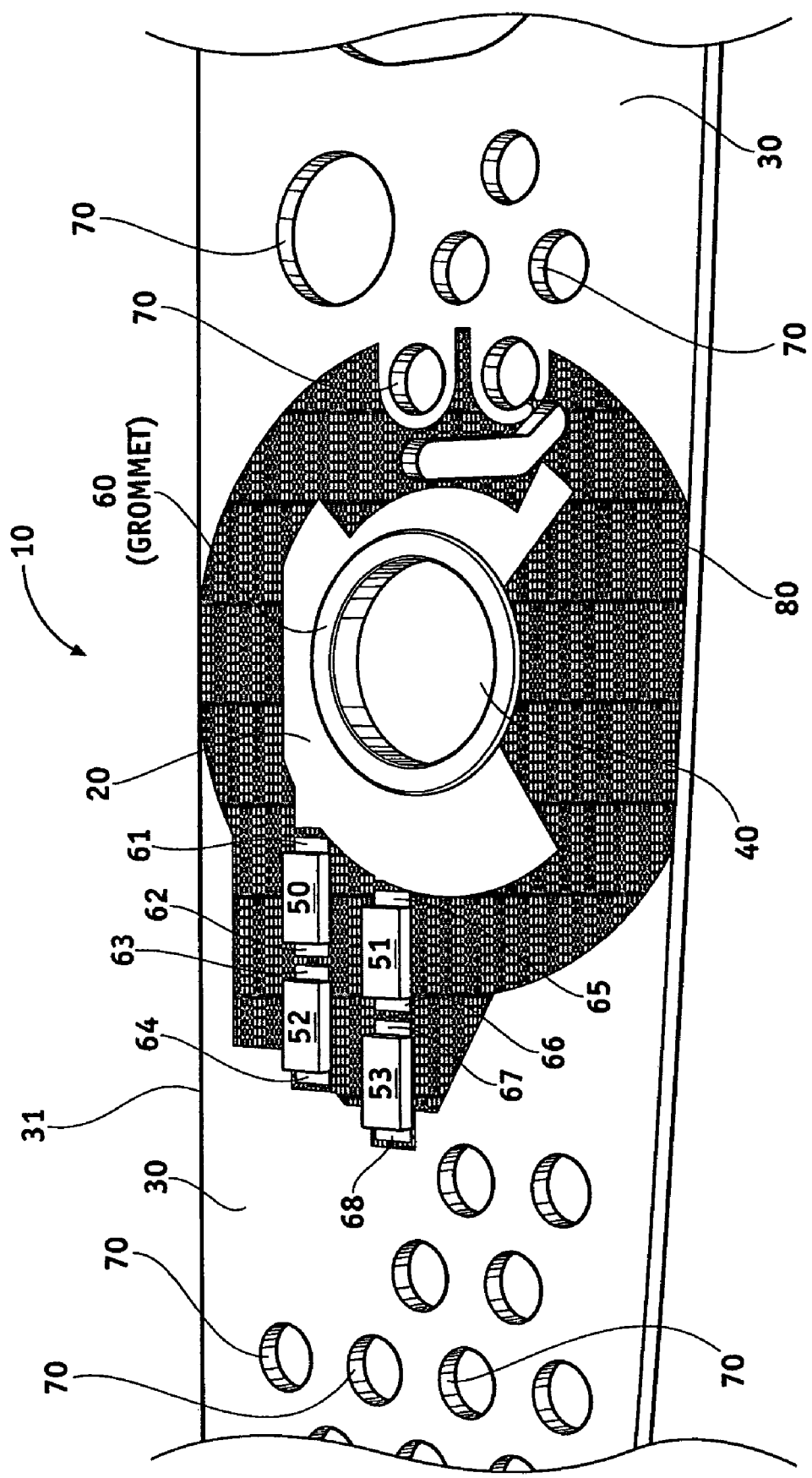

FIGS. 4 and 5 are plan and isometric views respectively of the interior surface of panel 10. Panel 10 includes an opening 40 configured to receive a connector coupled to the proximal end of cable 310 (shown in FIG. 1). An electrically non-conductive grommet 60 is positioned within opening 40 and may include a groove which is sized to fit over the edge of panel 10 in opening 40 thereby retaining grommet 60 in place. Grommet 60 made of an insulating material and is secured within opening 40 to prevent any connector extending through opening 40 from electrically contacting panel 10. An interior surface of panel 10 comprises a first conductive region 20 positioned substantially adjacent opening 40. As can be seen, conductive region 20 forms a partial ring around opening 40. The interior surface also comprises a second conductive region 30 spaced from conductive region 20 that covers substantially all the remaining portion of the interior surface of panel 10. Conductive region 30 is coupled to ground so as to attenuate electromagnetic radiation from the electronic circuitry within the device.

In a preferred embodiment, panel 10 may comprise a multi-layered printed circuit board containing alternate conductive layers separated by insulating layers. For example, panel 10 may comprise a four-layer printed circuit board having conductive layers on both major external surfaces and two-burried conductive layers between the external surfaces. The conductive surface on the interior surface of panel 10 comprises a pattern of conductive regions of the type previously described. A plurality of plated-through holes 70 electrically couple conductive region 30 to the other metal layers in the printed circuit board. Thus, an effective shield for attenuating EMI is formed. Openings 70 also provide for the passage of air to cool the electronic circuitry within the housing.

Conductive contact pads 61-68 are provided in non-conductive region 80 to serve as contacts for first and second terminals of each of capacitors 50, 51, 52, and 53. An intermediate conductive layer may be utilized to electrically couple contact pads 61 and 65 to conductive region 20, contact pads 64 and 68 to conductive region 30, contact 62 to contact 63, and contact 66 to contact 67. In this manner, capacitors 50-52 and 51-53 form parallel AC paths to ground from conductive region 20 to conductive region 30. These capacitors are rated for a specific voltage and provide low resistance above a predetermined frequency. This enhances attenuation of EMI for a particular electronic configuration.

Figure 6:
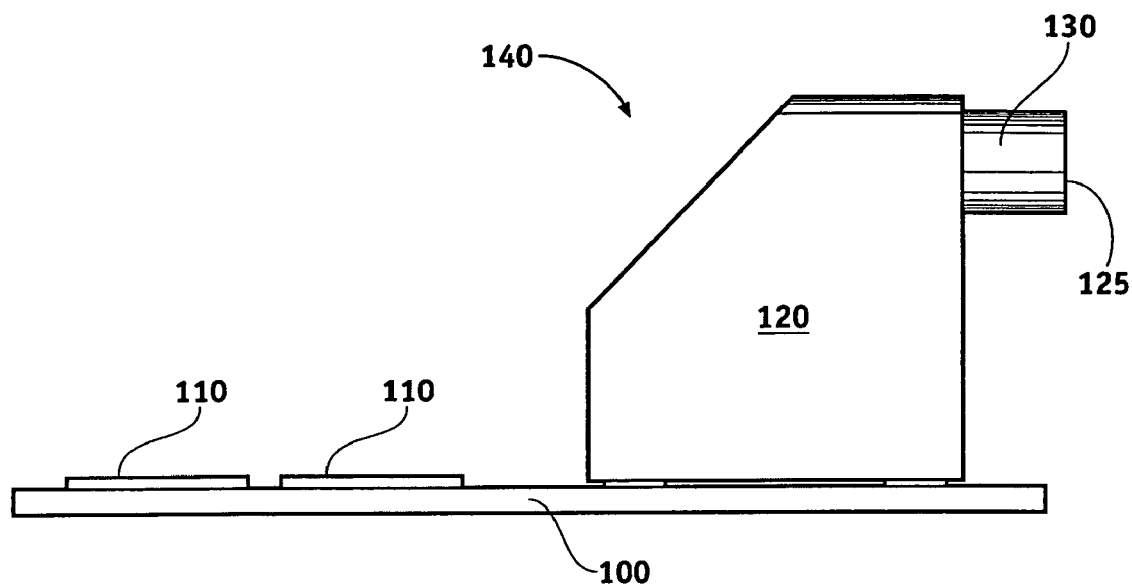
FIG. 6 is a side view of a portion of an electrical circuit/connector assembly shown in FIGS. 2 and 3.

FIG. 6 is a side view of a portion of the electrical circuit shown in FIGS. 2 and 3 and depict substrate 100, electrical components 110 mounted thereon, and connector 140 likewise mounted on substrate 100 and electrically coupled to circuitry on substrate 100 using well known techniques. Connector 140 includes a non-conductive cover 120 and a plug 125 that extends outward and beyond cover 120 and includes a conductive shield 130. That portion of plug 125 and conductive shield 130 that extends externally of cover 120 is configured to extend through opening 40 in panel 10 where it may be electrically coupled to a connector at the proximal end of cable 310 as is shown in FIG. 1. The use of conductive shield 130 also contributes to the attenuation of electromagnetic radiation from the connector terminal thus reducing the total EMI generated by the medical device.

Figure 7:
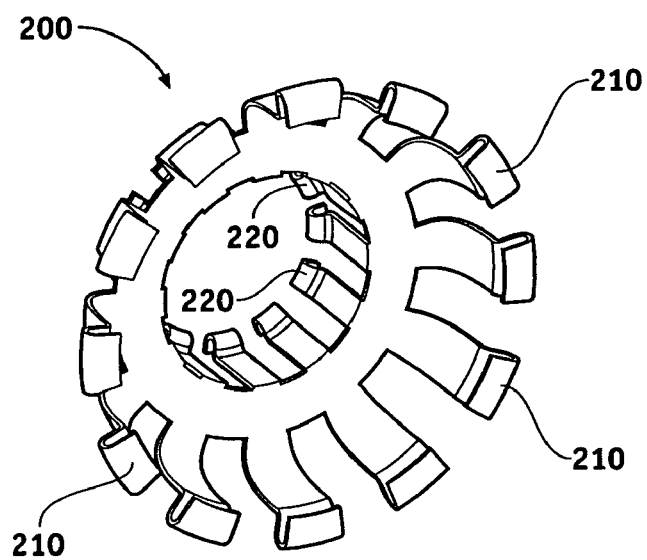
FIG. 7 is an isometric view of a clip shown in FIGS. 2 and 3 for coupling the connector shown in FIG. 6 to the panel shown in FIGS. 4 and 5.

FIG. 7 is an isometric view of clip 200 utilized to electrically couple connector 140 to conductive region 20 on panel 10. It can be seen that the clip comprises a first plurality of contacts 220 that extends in a first direction and is arranged in a generally circular configuration. A second plurality of contacts 210 extends in a generally opposite direction and is likewise assembled in a generally circular configuration. It can be seen that the diameter of the circular assembly of clips 220 is less than the diameter of the circular arrangement of clips 210. Contacts 220 form a circular opening that has a diameter that is slightly less than the outer diameter of conductive shield 130. Thus, contacts 220 expand outward when inserted over conductive shield 130 thereby creating a resilient tension that maintains clip 200 on conductive shield 130. As can be seen in FIG. 3, contacts 210 extend forward and contact conductive region 20 of panel 10. Since contacts 310 are resilient, good electrical contact with conductive region 20 is maintained. Connector 140 is a positioned on substrate 100 such that the plurality of contacts 210 on clip 200 are held in place.

While at least one exemplary embodiment has been presented in the foregoing detailed description, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient roadmap for implementing an exemplary embodiment or exemplary embodiments. It should be understood that various changes can be made in the function and arrangement of elements without departing from the scope of the invention as set forth in the appended claims and the legal equivalence thereof.

What is claimed is:

1. A medical device configured to attenuate emission of electromagnetic radiation, comprising:
    a housing formed by an enclosure and a panel having an interior surface, wherein said panel comprises a printed circuit board; and
    a circuit assembly mounted within said housing;
    said panel comprising:
        an opening through the panel to accept an electrical coupling to the circuit assembly, said opening having a non-conductive grommet;
        said interior surface having a first conductive region substantially surrounding the opening;
        said interior surface having a second conductive region, the second conductive region being spaced from the first conductive region;
        said interior surface having a non-conductive region between said first conductive region and said second conductive region; and
    means for providing a path to ground from the first conductive region and the second conductive region for radio frequency interference signals above a predetermined frequency.

2. A medical device according to claim 1 wherein said circuit assembly comprises:
    a plurality of circuit elements configured to generate a desired patient therapy;
    a connector plug electrically coupled to selected ones of said circuit elements; and
    a conductive shield coupled to said connector plug and AC coupled to ground for attenuating electromagnetic radiation from said plug.

3. A medical device according to claim 2 wherein said conductive shield is generally cylindrical and includes a portion that extends at least into said opening.

4. A medical device according to claim 3 further comprising a conductive clip for coupling said conductive shield to said first conductive region.

5. A medical device according to claim 4 wherein said clip comprises:
    a first plurality of contacts extending in a first direction for resiliently engaging said conductive shield; and
    a second plurality of contacts extending in a second direction for resiliently engaging said first conductive region.

6. A medical device according to claim 5 wherein said first plurality of contacts are configured to form a substantially circular opening through said clip for receiving said conductive shield.

7. A medical device configured to attenuate emission of electromagnetic radiation, comprising:
- a housing formed by an enclosure and a panel having an interior surface;
- a circuit assembly including a connector plug mounted in said panel;
- said panel being coupled to said electrical circuit assembly, said panel comprising:
  - an interior surface having a first conductive region; and
  - an opening substantially surrounded by said first conductive region;
  - said interior surface having a second conductive region; and
  - a non-conductive region on said interior surface between said first conductive region and said second conductive region;
- at least one capacitor electrically coupled between said first conductive region and said second conductive region;
- a conductive shield coupled to said connector plug; and
- a conductive clip electrically coupling said conductive shield to said first conductive region.

8. A medical device according to claim 7 wherein said panel comprises a multilayered printed circuit board.

9. A medical device according to claim 8 wherein said multilayered printed circuit board comprises an exterior surface and at least one conductive layer between said interior surface and said exterior surface and electrically insulated therefrom, and wherein a plurality of plated through holes electrically couple said second conductive region, said at least one conductive layer, and said exterior surface.

10. A medical device according to claim 9 further comprising at least one capacitor electrically coupled between said first conductive region and said second conductive region.

11. A medical device according to claim 10 comprising a non-conductive grommet through said opening.

12. A medical device according to claim 11 wherein said conductive shield is generally cylindrical and includes a portion that extends at least into said opening.

13. A medical device according to claim 12 wherein said clip comprises:
- a first plurality of contacts extending in a first direction for resiliently engaging said conductive shield, said first plurality of contacts configured to form a substantially circular opening through said clip for receiving said conductive shield; and
- a second plurality of contacts extending in a second direction for resiliently engaging said first conductive region.

* * * * *